United States Patent [19]
McDowall et al.

[11] Patent Number: 5,876,388
[45] Date of Patent: Mar. 2, 1999

[54] LIQUID DISTRIBUTION LAYER FOR ABSORBENT ARTICLES

[75] Inventors: Debra Jean McDowall, Roswell; Ruth Lisa Levy, Sugar Hill; Lawrence Howell Sawyer, Roswell; Susan Carol Paul, Alpharetta; Jay Sheldon Shultz, Roswell; Robert David Wright, Peachtree City; Eugenio G. Varona, Marietta, all of Ga.

[73] Assignee: Kimberly-Clark Worldwide, Inc., Neenah, Wis.

[21] Appl. No.: 603,023

[22] Filed: Feb. 16, 1996

Related U.S. Application Data

[63] Continuation of Ser. No. 220,892, Mar. 31, 1994, abandoned.

[51] Int. Cl.[6] .................................................. A61F 13/15
[52] U.S. Cl. ........................................ 604/384; 604/358
[58] Field of Search .................................. 604/358, 367, 604/378, 384

[56] References Cited

U.S. PATENT DOCUMENTS

| | | |
|---|---|---|
| 3,119,152 | 1/1964 | Kalwaites . |
| 3,379,811 | 4/1968 | Hartmann et al. . |
| 3,602,224 | 8/1971 | Abee ........................................ 604/384 |
| 3,612,055 | 10/1971 | Mesek . |
| 3,689,342 | 9/1972 | Vogt et al. . |
| 3,752,613 | 8/1973 | Vogt et al. . |
| 3,768,118 | 10/1973 | Ruffo et al. ............................. 19/156.3 |
| 3,772,417 | 11/1973 | Vogt . |
| 3,849,241 | 11/1974 | Butin et al. . |
| 3,865,112 | 2/1975 | Roeder . |
| 3,993,820 | 11/1976 | Repke ....................................... 428/167 |
| 3,997,647 | 12/1976 | Lassen . |
| 4,018,646 | 4/1977 | Ruffo et al. ............................. 162/146 |
| 4,073,852 | 2/1978 | Mesek . |
| 4,189,512 | 2/1980 | Ellis et al. . |
| 4,223,677 | 9/1980 | Anderson . |
| 4,256,111 | 3/1981 | Lassen ..................................... 128/284 |
| 4,360,022 | 11/1982 | Usami et al. . |
| 4,443,513 | 4/1984 | Meitner et al. . |
| 4,480,000 | 10/1984 | Watanabe et al. . |
| 4,559,050 | 12/1985 | Iskra . |
| 4,631,062 | 12/1986 | Lassen et al. . |
| 4,636,209 | 1/1987 | Lassen . |
| 4,655,760 | 4/1987 | Morman et al. . |
| 4,676,786 | 6/1987 | Nishino .................................... 604/378 |
| 4,699,619 | 10/1987 | Bernardin . |
| 4,714,647 | 12/1987 | Shipp, Jr. et al. . |
| 4,797,318 | 1/1989 | Brooker et al. . |
| 4,865,596 | 9/1989 | Weisman et al. . |
| 4,908,026 | 3/1990 | Sukiennik et al. . |
| 4,910,064 | 3/1990 | Sabee . |
| 4,948,639 | 8/1990 | Brooker et al. . |
| 4,965,122 | 10/1990 | Morman . |
| 4,966,808 | 10/1990 | Kawano . |
| 5,037,409 | 8/1991 | Chen et al. ............................... 604/358 |
| 5,051,159 | 9/1991 | Togashi et al. . |
| 5,156,905 | 10/1992 | Bagrodia et al. . |
| 5,188,624 | 2/1993 | Young, Sr. et al. . |
| 5,200,248 | 4/1993 | Thompson et al. . |

FOREIGN PATENT DOCUMENTS

0403840  12/1990   European Pat. Off. .

*Primary Examiner*—John G. Weiss
*Assistant Examiner*—Dennis Ruhl
*Attorney, Agent, or Firm*—Michael U. Lee; James B. Robinson

[57] ABSTRACT

The present invention provides a liquid distribution layer for absorbent articles which exhibits directional liquid distribution properties and has desirable physical integrity. The liquid distribution layer is a nonwoven web of substantially continuous microfibers that has its fibers substantially aligned along one planar dimension of the web, wherein the fibers are hydrophilically modified or hydrophilic. Additionally, the liquid distribution layer may have an increasing fiber alignment gradient as well as a decreasing fiber thickness gradient in the direction of the web thickness. Further provided are suitable processes for producing the liquid distribution layer.

4 Claims, 5 Drawing Sheets

LIQUID DISTRIBUTION LAYER FOR ABSORBENT ARTICLES

This application is a continuation of application Ser. No. 08/220,892 entitled "LIQUID DISTRIBUTION LAYER FOR ABSORBENT ARTICLES" and filed in the U.S. Patent and Trademark Office on Mar. 31, 1994 now abandoned. The entirety of this application is hereby incorporated by reference.

The present invention relates to a liquid distribution layer for absorbent articles, particularly for diapers, sanitary napkins, training pants, incontinent care pads, wound dressings and the like.

Conventional absorbent articles typically have an absorbent core containing cellulosic fibers, e.g., wood pulp fluffs; particles of highly absorbent materials, e.g., superabsorbents; and an admixture of cellulosic fibers and superabsorbents. Recently, the use of absorbent cores of admixtures of cellulosic fibers and superabsorbent particulates that have high content of superabsorbent materials has been gaining wide popularity from the fact that such absorbent cores provide improved absorbent capacities without increasing or while reducing the bulk of the cores. Although high superabsorbent content absorbent cores have high capacities for liquid absorption, they, however, do not exhibit adequate liquid wicking and distribution properties. Consequently, the utilization of the absorbent material in a compact absorbent article is limited to the region where the material is in contact with incoming liquid, e.g., exudate or urine, and to the lowest portion of the absorbent article, where the liquid collects due to gravitational flow, resulting in underutilization of the absorbent material located at remote and/or high portions of the absorbent article. Therefore, a better distribution of incoming liquids would promote an efficient use of the absorbent material and prevent premature failures of the absorbent article.

There have been many attempts to improve the liquid distribution function of absorbent articles. One such attempt is placing a liquid distribution layer adjacent to the absorbent material of an absorbent article. For example, U.S. Pat. No. 4,360,022 to Usami et al. discloses a sanitary napkin having an unbonded tow of hydrophobic filaments over the absorbent core. However, such use of hydrophobic filament tow layers has not been fully satisfactory. Although the hydrophobic layer may distribute liquid in the direction of length of the tow in relatively horizontal positions, the hydrophobic nature of the tow layer tends to hinder rapid intake of the incoming liquids and does not facilitate the movement of liquid against gravity in a vertical direction. An alternative approach is placing an unbonded tow or web of hydrophilic filaments, especially fine filaments to provide softness and flexibility, over the absorbent core. The use of hydrophilic fine filament tow has not been fully satisfactory, either. Unbonded hydrophilic filaments of a tow, which although at first rapidly absorb incoming liquids, tend to collapse when the filaments become wet, collapsing the capillary walls between the filaments and preventing the liquids from moving downward through the filaments toward the absorbent material. Moreover, unbonded tows of hydrophilic or hydrophobic filaments tend to shift or bundle during shipment and use, and to have loose or stray filaments, creating difficulties in the absorbent article manufacturing process and causing uneven liquid distribution patterns in finished absorbent articles. In addition, filament tows, which are produced from a multi-stage manufacturing process, are relatively expensive.

In the relevant art, it is known that fine fibers facilitate capillary movements of liquid and that certain melt-processed fiber webs can be produced to have fine fibers. However, melt-processed nonwoven fiber webs of fine fibers have their limitations. This is because conventional melt-processed nonwoven fiber webs, which are designed and produced to have an isotropic fiber arrangement, i.e., fibers are randomly dispersed to produce nonwoven webs of multi-directional physical integrity, are not highly conducive to moving liquid in a desired direction and do not efficiently promote high levels of liquid capillary movements. In addition, most of the melt-processable thermoplastic polymers are inherently hydrophobic, and thus fiber webs made therefrom do not provide any significant capillary movements and wicking actions, especially against gravity.

Consequently, it would be desirable to provide a dimensionally stable liquid distribution layer that can quickly transfer incoming liquids even to remote areas of the absorbent material of an absorbent article and away from the source of the incoming liquids by providing high degrees of directional capillary movement and wicking actions even against gravity.

SUMMARY OF THE INVENTION

The present invention provides a liquid distribution layer for absorbent articles which exhibits directional liquid distribution properties and has desirable physical integrity. The liquid distribution layer is a nonwoven web of substantially continuous microfibers that has its fibers substantially aligned along one planar dimension of the web, wherein the fibers are produced from a polymer selected from the group consisting of hydrophilically modified polymers and hydrophilic polymers. Additionally, the liquid distribution layer may have an increasing fiber alignment gradient as well as a decreasing fiber thickness gradient in the direction of the web thickness.

The present invention further provides a process for producing the liquid distribution layer for absorbent articles. The process includes the steps of providing a stream of gas-borne microfibers from a fiber spinning apparatus and depositing the stream of gas-borne microfibers onto a forming surface at an acute angle. The liquid distribution layer production process may contain more than one fiber spinning apparatus in sequence such that the liquid distribution layer may additionally contain a fiber thickness gradient and/or a fiber orientation gradient across its thickness. The gradient containing layer is produced from a process having the steps of depositing a first stream of first gas-borne microfibers at a first acute angle onto a forming surface to form a nonwoven fiber web, and depositing a second stream of second gas-borne microfibers at a second acute angle onto the first fiber web, wherein the first acute angle is smaller than the second acute angle and the first gas-borne microfibers have a smaller average fiber size than the second gas-borne microfibers.

The present invention also provides a process for producing the liquid distribution layer from a fully formed microfiber web. The process contains the steps of heating a thermoplastic microfiber web to a temperature between the softening point and the melting point of the fiber web, applying a tensioning force to neck the heated fiber web, and cooling the necked fiber web while maintaining the tensioning force.

Additionally provided is an absorbent article containing a liquid-permeable facing layer, a liquid distribution layer, an absorbent core and a liquid-impermeable backing layer. The liquid distribution layer of the absorbent article contains a nonwoven web of substantially continuous microfibers, and the microfibers of the web are produced from a polymer selected from the group consisting of hydrophilically modified polymers and hydrophilic polymers, and are substantially aligned along one planar dimension of the web.

The liquid distribution layer of the present invention promotes rapid removal of incoming liquid and directionally distributes the liquid over a wide area away from the source.

DETAILED DESCRIPTION OF THE INVENTION

There is provided in accordance with the present invention a liquid distribution layer for absorbent articles. The distribution layer is an anisotropic nonwoven fiber web of substantially continuous microfibers produced from a fiber-forming polymer, in which the fibers of the nonwoven web are hydrophilically modified and substantially aligned along one desired direction of the web, e.g., in the machine direction (MD) or cross-machine direction (CD) of the web.

In accordance with the present invention, the level of fiber alignment of a nonwoven web is measured by the fiber alignment ratio, which is defined as the relative fibers alignment in the MD or CD over the relative fiber alignment in the other direction. Desirably, suitable microfiber web of the present liquid distribution layers have a fiber alignment ratio of at least about 4:1, more desirably at least 10:1, most desirably at least 30:1, having the fibers prominently oriented in either the MD or CD. The fiber alignment ratio is determined by measuring the sonic modulus of a nonwoven web in the MD and CD in accordance with ASTM F89-68, titled "Standard Method of Test for Modulus of a Flexible Barrier Materials by Sonic Method", and calculating the ratio therebetween. Briefly described, the determination of the fiber alignment ratio is based on the fact that a sonic modulus is proportionally related to fiber alignment in planar directions and the ASTM F89-68 testing procedure provides means for evaluating the sonic modulus of a flexible material in planar directions by measuring the velocity of longitudinal sound waves through the material.

The present anisotropic microfiber web provides high dimensional stability and physical integrity and highly improved liquid distribution properties in that the hydrophilically modified aligned fibers of the present fiber web, which are strongly entangled and/or form strong interfiber bonds, facilitate capillary and wicking movements of liquid substantially along the direction of the fiber alignment without the problems of prior art liquid distribution layers such as loose and shifting filaments. Highly useful liquid distribution layers of the present invention desirably have a weight of from about 0.1 ounce per square yard (osy) to about 15 osy, more desirably from about 1 osy to about 5 osy, and a thickness of from about 0.001 inches to about 0.5 inches, more desirably from about 0.008 inches to about 0.15 inches.

Figure 1:
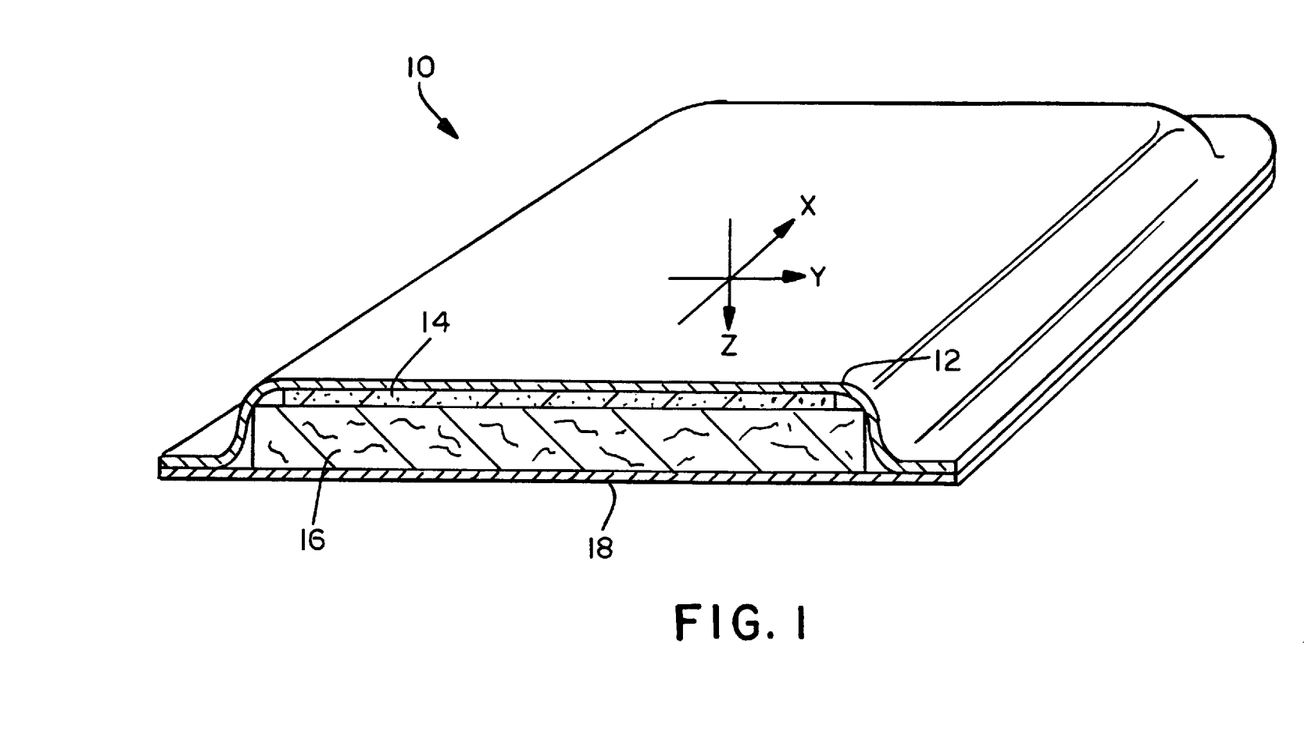
FIG. 1 illustrates a use of the liquid distribution layer on an absorbent article.

FIG. 1, which is a cross-sectional view of an absorbent article 10, provides an exemplary use of the present liquid distribution layer. The absorbent article 10 contains a liquid-permeable facing layer 12, a liquid distribution layer 14, an absorbent core or body 16 and a liquid-impermeable layer 18. The liquid distribution layer 14 is in intimate contact with both the absorbent core 16 and the facing layer 12. The liquid distribution layer 14 distributes incoming body fluids in the x- and y-planar directions, mostly along the direction of fiber orientation, as well as in the z-direction, i.e., the depth of the layer, thereby better and efficiently utilizing the absorbent capacity of the absorbent core 16. Although FIG. 1 illustrates the placement of the liquid distribution layer as being placed on the absorbent core 12, the liquid distribution layer may alternatively be placed underneath the absorbent core or placed on both the top and the bottom of the absorbent core, or placed between two layers of an absorbent material in order to accommodate different design and functional criteria of absorbent articles. The facing layer 12 is designed to rapidly intake liquids applied thereupon and to pass the liquids onto the liquid distribution layer 14. The facing layer 12 may be a nonwoven or woven fabric, perforated film or nonwoven, or any other relatively porous material that is known to rapidly pass liquid. The backing layer 18 may be any desirable liquid-impermeable material that can prevent liquid absorbed by the absorbent core 16 from migrating outside the absorbent article. The backing layer may be vapor-permeable. Illustrative of suitable materials are thermoplastic films, such as polyethylene films. The absorbent core 16 may be fabricated from any highly liquid absorbent material known in the art, including natural organic materials, e.g., cellulosic fluffs, agar, pectin and guar gum; synthetic hydrogel polymers, e.g., carboxymethylcellulose, metal salt of polyacrylic acids, polyacrylamides, polyvinyl sulfonic acids, polyacrylates, polyacrylamide and the like; as well as mixtures thereof.

The present anisotropic liquid distribution web may additionally be engineered to have a fiber thickness gradient, a fiber alignment gradient or a combination of the two gradients. It has been found that the level of fiber alignment controls the directional liquid distribution properties. An anisotropic web having a higher fiber alignment level exhibits a higher liquid distribution property in the direction of fiber alignment. It has also been found that providing a fiber thickness gradient improves liquid intake and distribution properties of an anisotropic web. In general, fibers having a larger fiber thickness tend to create a lower density region having large interstitial openings that promote fast intake of incoming liquids while fibers having a smaller fiber thickness tend to create denser, smaller pore regions that facilitate capillary movements, wicking actions and distribution functionalities. Consequently, by selecting proper combinations of the fiber orientation gradient and fiber thickness gradient, different needs of different absorbent article applications can be accommodated with improved and particularized functionalities. For example, a highly useful liquid distribution layer can be created to have a decreasing fiber thickness gradient and an increasing fiber orientation gradient in the z-direction toward the absorbent body, i.e., in the direction of the liquid distribution layer thickness, such that incoming liquids are rapidly taken up by the upper portion of the layer and widely distributed by the lower portion of the layer, thereby rapidly and efficiently distributing incoming liquid over a wide area of the absorbent core.

As stated above, the liquid distribution layer is a nonwoven fiber web fabricated from substantially continuous microfibers of a fiber-forming polymer. Nonwoven fiber webs suitable for the present invention include microfiber webs having relatively strong interfiber bonds or entanglement, such as meltblown fiber webs, melt-sprayed fiber webs, solution-sprayed fiber webs and the like. The fibers for suitable fiber webs may be homocomponent fibers or multicomponent conjugate fibers. As used herein, the term "microfibers" indicates small diameter fibers having an average diameter not greater than about 25 $\mu$m, for example, having an average diameter of from about 0.5 $\mu$m to about 25 $\mu$m, and more particularly, an average diameter of from about 1 $\mu$m to about 15 $\mu$m. The term "substantially continuous fibers" includes continuous fibers and relatively lengthy fibers that have an average length longer than the average length of typical natural and synthetic staple fibers. The term "meltblown fiber web" or "melt-spray fiber web" indicates a fiber web formed by extruding a molten thermoplastic polymer through a spinneret containing a plurality of fine, usually circular, die capillaries as molten filaments or fibers into a high velocity gas stream which attenuates or draws the filaments of molten thermoplastic polymer to reduce their diameter. In general, meltblown fibers have an average fiber diameter of up to about 10 $\mu$m, although thicker meltblown fibers can be produced. After the fibers are formed, they are carried by the high velocity gas stream and are deposited on a forming surface to form an autogenously bonded web of randomly disbursed, highly entangled meltblown microfibers. Such a process is disclosed, for example, in U.S. Pat. No. 3,849,241 to Butin. The term "solution-sprayed fiber web" refers to a fiber web formed by pumping an organic or aqueous solution of a fiber-forming polymer into a high velocity gas stream to form gas-borne fibers and directing the fibers in a continuous or semi-continuous stream onto a forming surface while removing major portions of the solvent to form substantially solid fibers and to form a highly entangled, autogenously bonded fiber web. These microfiber webs, having autogenously bonded or entangled fine fibers, provide a web structure that is highly conducive to directional liquid wicking actions and capillary movements when the fibers are substantially aligned to a desired direction.

In accordance with the present invention, aligning the fibers of a nonwoven microfiber web can be effected by a number of different processes that impart fiber alignment during or after the formation of the fiber web. One group of suitable processes effect the fiber alignment during the formation of the web by directing the drawn fibers to be deposited onto a forming surface at an acute deposit angle, desirably at an angle from about 10° to about 80°, more desirably from about 15° to about 60°. In general, a smaller deposit angle produces a more highly oriented web. However, as the deposit angle becomes too small, depositing gas-borne fibers onto the forming surface becomes difficult due to high scattering of the fibers. According to the present invention, suitable fiber directing or depositing processes should direct the stream of gas-borne fibers with minimal dispersion before the fibers reach the forming surface, and such suitable processes include airknife orientation processes and acute-angle depositing processes.

Figure 2:
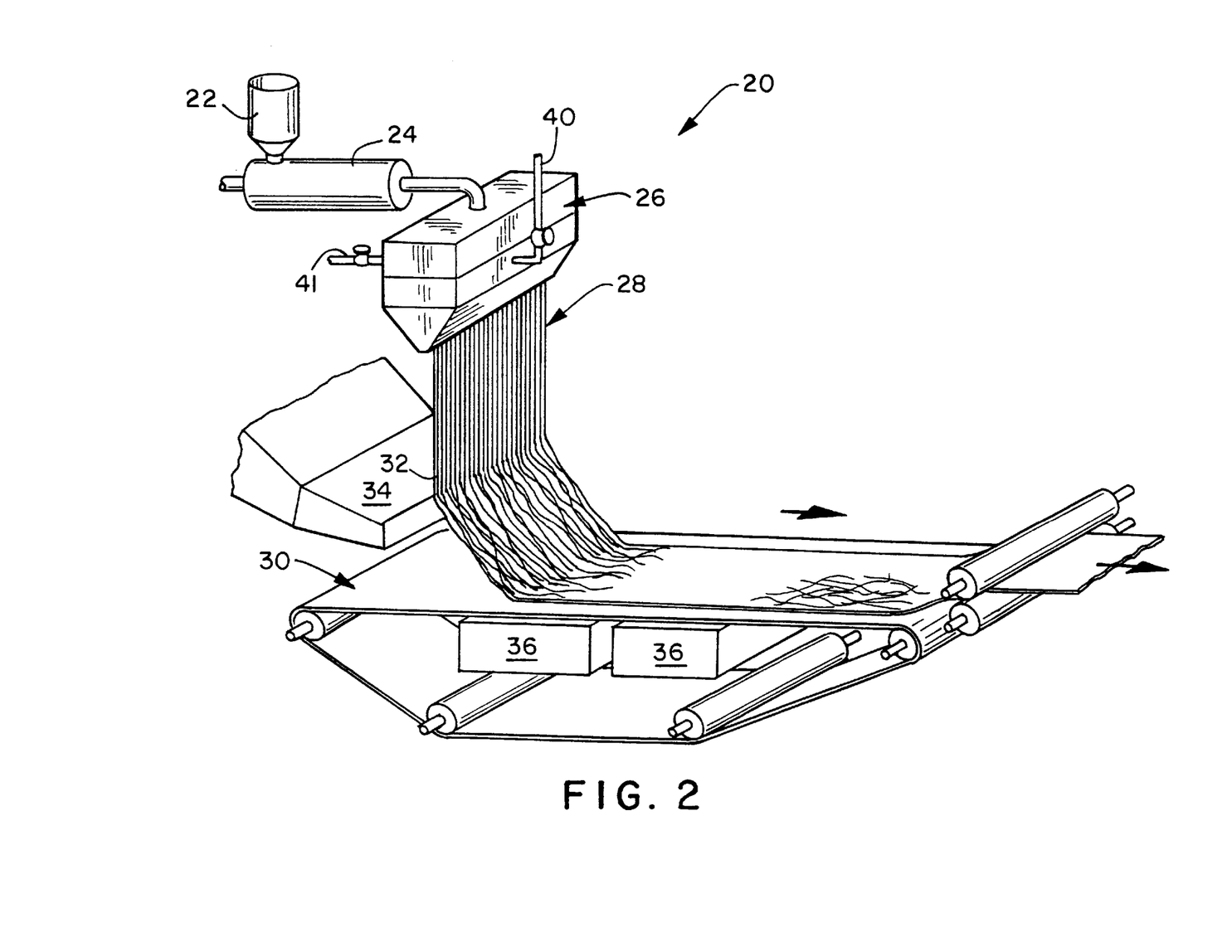
FIG. 2 illustrates an exemplary airknife process of producing the liquid distribution layer.

An airknife orientation process suitable for the present invention is disclosed in a commonly assigned copending patent application Ser. No. 07/864,808, filed Apr. 7, 1992, which is hereby incorporated by reference. An airknife orientation process employs a secondary gas stream between the spinneret and the web forming surface to direct or deflect, with minimal dispersion, the stream of gas-borne fibers approaching the forming surface in such a way that the center of the fiber stream and the forming surface form an acute angle. FIG. 2 illustrates an exemplary airknife process 20 that may be utilized to produce the anisotropic webs of the present invention. For purposes of illustration, the process is represented with a meltblown fiber web forming process. Pellets or chips of a suitable polymer are introduced to a hopper 22 and melt-extruded through an extruder 24. The molten polymer is pumped through a heated meltblowing spinneret or capillary die 26, which is equipped with an attenuating gas stream, to form filaments or fibers. The attenuating gas stream, which is supplied through an inlet 40 or inlets 40–41 and typically is a heated gas, entrains and attenuates the spun fibers 28. The pressure of the gas may be adjusted so that it is powerful enough to attenuate the extruded filament into fine fibers and yet avoid undesirable dispersion and scattering of the fibers when the fibers are collected onto a forming surface 30 to form a coherent nonwoven web. The dispersion and scattering of the fibers can be further reduced by placing a vacuum source 36 below the forming surface 30 where the stream of gas-borne fibers comes in contact with the forming surface. In accordance with the present invention, the stream of fibers 28 is impinged by a deflecting gas stream 32 that is supplied by a gas supplying device 34. The deflecting gas stream 32 deflects the path of the fiber stream 28, causing the fibers to be deposited at an acute angle onto the forming surface 30. The pressure and flow rate of the deflecting gas stream is maintained at a level sufficient to cause the stream of gas-borne fibers to deflect, but not too high as to cause high turbulence and scattering of the fibers. For example, the pressure of the attenuating gas may range from about 0.25 to about 15 pounds per square inch (psi), gauge, particularly from about 0.5 to about 5 psi, at the point where the deflecting gas stream is applied, and the pressure of the deflecting gas may range from about 2 to about 10 inches of water column, and the velocity may range from about 2,000 to about 16,000 feet per minute. Alternatively, the deflecting gas may be applied as a high pressure, low volume stream similar to the attenuating gas stream. The deflecting gas may be any gas that does not adversely affect the properties of the fibers, and the gas stream may contain additives, which topically treat the spun fibers, or other materials, such as other fibers and fillers, that may be added to impart modified properties in the resulting fiber web.

The deflecting gas stream is applied in the same direction as the running direction of the forming surface, and the discharging point of the deflecting gas stream is closely placed next to one side of the stream of gas-borne fibers 28 between the forming surface 30 and the spinneret 26. It is desirable that the gas discharging point, where the deflecting gas impacts the gas-borne fiber stream, is located such that the deflected stream has only a minimum distance to travel to reach the forming surface in order to minimize dispersion of the entrained spun fibers. For example, the deflecting gas discharging point may be located from about 1.5 to about 5 inches off to one side of the gas-borne fiber stream and from about 2 to about 12 inches from the forming surface. In general, the dispersion of the spun fibers is minimized and correspondingly the alignment of the fibers is improved when the fiber forming distance, i.e., the distance between the spinneret and the forming surface, is minimized. In order to facilitate a shorter fiber forming distance, it may be desirable to utilize a cooled deflecting gas to accelerate the quenching of the spun fibers. In addition, a vacuum apparatus can be placed underneath the fiber depositing portion of the forming surface to minimize the dispersion of the gas-borne fibers. More desirably, the fiber alignment process can be better facilitated by profiling a series of varying vacuum pressures from low to high in the direction of the forming surface advancement.

The anisotropic webs of the present invention can alternatively be produced by an acute-angle depositing process. A conventional fiber web forming process is modified by altering the position of the forming surface and/or the discharging angle of the spinneret. In accordance with the present invention, the forming surface is placed to form an acute angle with the fiber stream exiting the spinneret, instead of the conventional horizontal placement of the forming surface that forms a fiber depositing angle of about 90°. Alternatively, the same result can be achieved by rotating the spinneret in the direction of advancement of the forming surface so that the fiber stream and the forming surface, again, form an acute angle.

Figure 3:
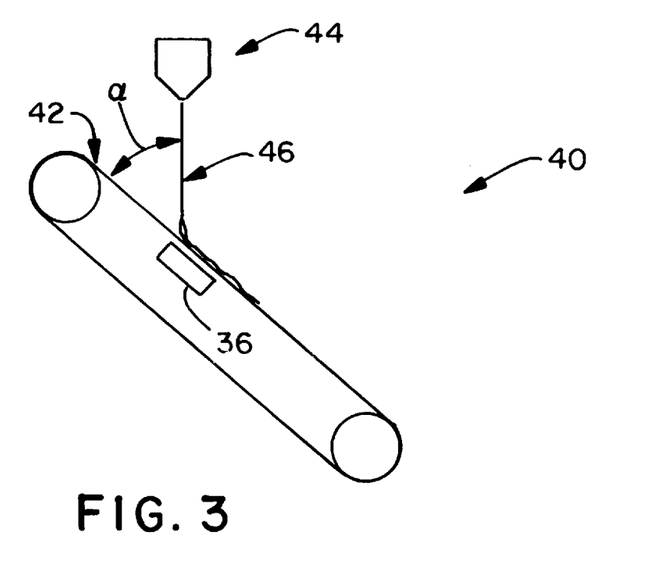
FIGS. 3 and 4 illustrate examples of the acute angle depositing process for producing the liquid distribution layer.
Figure 4:
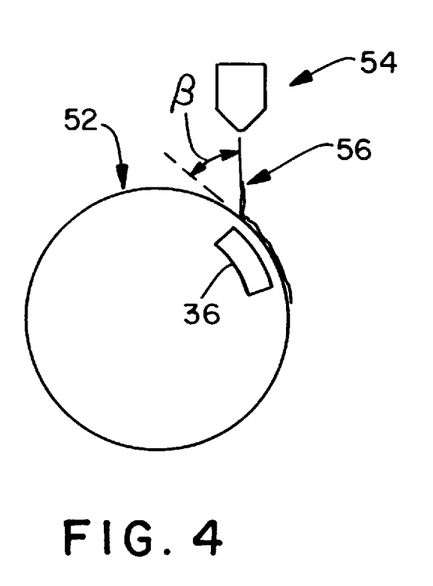

Illustrative examples of the acute-angle depositing processes are shown in FIGS. 3 and 4. In FIG. 3, a fiber web forming apparatus 40 containing a forming surface 42 and a fiber spinneret 44 is modified by realigning the forming surface 42 and/or the spinneret 44 in such a way that the forming surface 42 and the fiber stream 46 exiting the spinneret 44 form an acute angle α. In FIG. 4, a circular forming surface 52 is utilized and the spinneret assembly 54 is placed off center of the circular forming surface 52 such that the stream of fibers 56 and the tangential line of the forming surface at the point of fiber contact form an acute angle, β. The impingement angles α and β can be adjusted to impart different levels of fiber orientation in the resulting nonwoven webs. Desirably, the impingement angles α and β are in the range between about 10° and about 80°, more desirably between about 15° and about 60°. As in a conventional fiber web forming process, a vacuum apparatus 36 can be placed underneath the fiber depositing portion of the forming surface to facilitate a proper placement of the spun fibers. More desirably, again, the fiber alignment process can be better facilitated by profiling a series of varying vacuum pressures from low to high in the direction of the forming surface advancement.

As an alternate embodiment of the present invention, the alignment or orientation of the fibers of nonwoven webs can be effected after the webs are fully formed. An isotropic nonwoven fiber web, i.e., a fiber web having no significant orientation in its fiber placement, can be mechanically worked or neck-stretched to render it anisotropic. A neck-stretching process suitable for the present invention is disclosed in a commonly assigned copending patent application Ser. No. 07/990,161, filed Dec. 14, 1992, which is hereby incorporated by reference. Generally, when melt-processed nonwoven fiber web is neck-stretched, this method includes the steps of (1) plasticizing a nonwoven fiber web by heating the web to a temperature above the softening point but below the melting point of the component polymer of the web; (2) applying a tensioning force to neck or stretch the heated nonwoven web, so that the fibers in the web are substantially aligned in the tensioned direction; and (3) de-plasticizing the necked nonwoven web by cooling the web while maintaining the tensioning force, so that the aligned fibers of the web retain their anisotropic orientation. Alternatively, when solution-sprayed fiber web is neck-stretched, this method includes the steps of (1) plasticizing a solution-sprayed fiber web by applying a suitable solvent, e.g., the solvent that was used to spin the fiber web; (2) applying a tensioning force to neck or stretch the plasticized nonwoven web, so that the fibers in the web are substantially aligned in the tensioned direction; and (3) de-plasticizing the web by removing the applied solvent while maintaining the tensioning force. The term "plasticizing" as used herein indicates making the fibers soft and malleable such that the fibers can be worked or stretched.

Although the extent of necking or stretching may vary to accomplish a desired level of fiber orientation and is only limited by web fracture, it is desirable to have the nonwoven web neck-stretched in the range of about 15% up to about 75%. The extent of stretching, as used herein, is calculated by dividing the difference in width between the initial sample and the necked sample by the initial sample width. In addition to providing the desired fiber alignment of a nonwoven web, the neck-stretching process, depending on the extent of stretch, may also be used to selectively draw the fibers, thereby increasing the total surface area and thus further improving the directional liquid distribution and wicking properties of the web.

Figure 5:
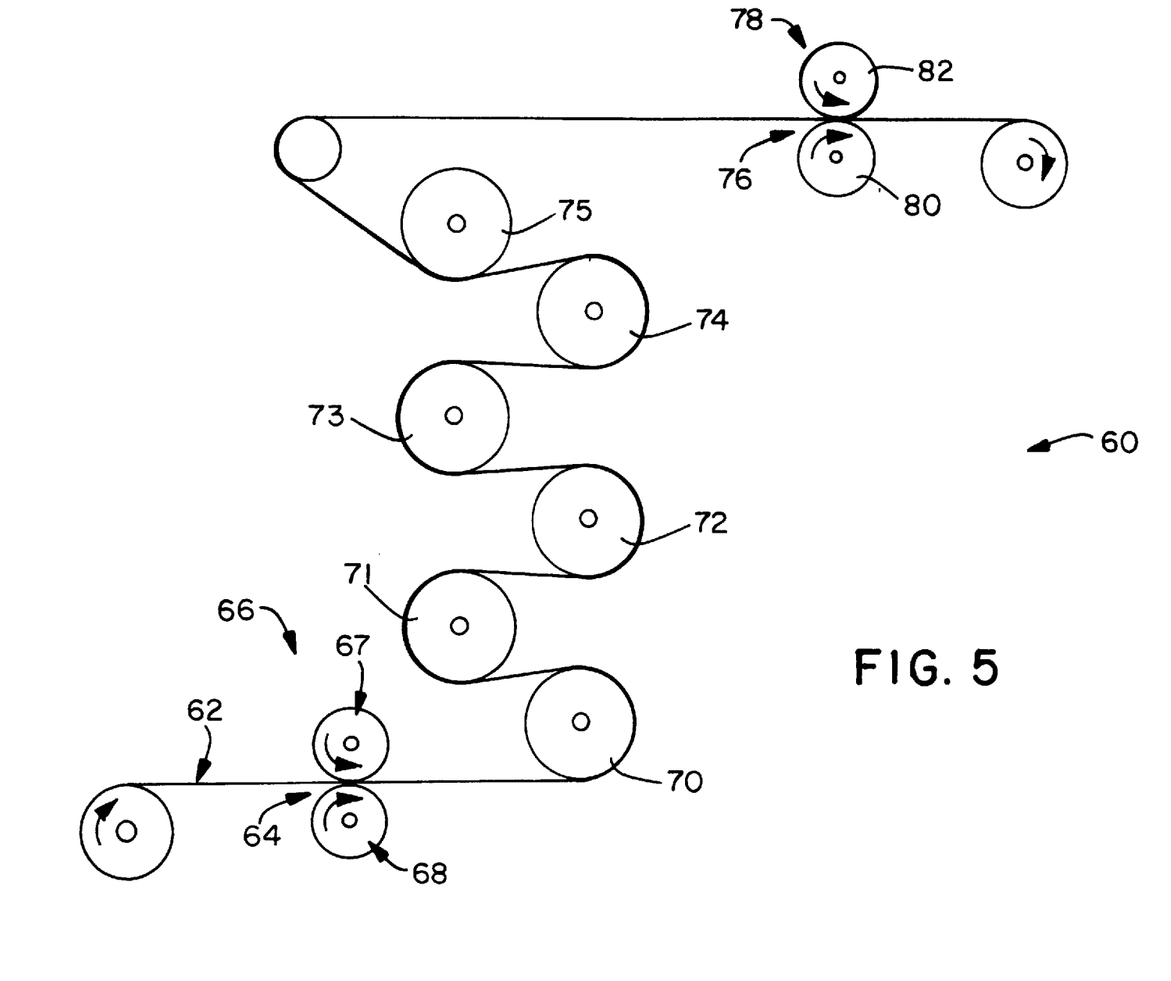
FIG. 5 illustrates an exemplary neck-stretching process.

Referring to FIG. 5, there is illustrated an exemplary process 60 for making a neck-stretched fiber web. A nonwoven web 62 is supplied from a supply roll to the nip 64 of a first roller arrangement 66 formed by the stack rollers 67 and 68. From the roller arrangement 66, the web 62 passes over a series of heated rolls 70–75 in a series of reverse S-loops to heat the web 62 to an appropriate temperature, i.e., the softening temperature of the web. The temperature of the heated rolls and the residence time of the web will vary depending on the type and basis weight of the web. For example, a meltblown polypropylene fiber web may be passed over a series of steam cans heated to a surface temperature from about 90° C. to about 150° C. for a contact time of about 1 to about 300 seconds to heat the web to a temperature above its softening point. Other suitable nonwoven web heating processes that can be utilized herein include infra-red radiation, heated fluid, heated air, microwaves, ultrasonic energy, convection oven and the like. The heated web 62 is then passed through the nip 76 of a second roller arrangement 78 formed by two stack rollers 80 and 82. The peripheral linear speed of the first roller arrangement 66 is controlled to be less than the peripheral linear speed of the second roller arrangement 78 so as to apply a neck-stretching tension. By controlling the linear speed differential between the two roller arrangements 66 and 78, the heated web 62 can be necked to a desired extent. Optionally, the heated rollers 70–75 can be controlled to have a linear speed or a series of linear speeds that are intermediate of the speeds of the two roller arrangements in order to facilitate the neck-stretching process. In addition to the roller arrangements, other tension applying methods and apparatus known in the art can be utilized, for example, tenter frames and godet rolls. The neck-stretched web is maintained under tension until it is cooled to retain the aligned configuration. The cooling process may be enhanced by the use of chilled air or chill rolls.

As another embodiment of the present invention, two or more of the above-described fiber alignment processes can be applied in combination to further enhance the fiber alignment of a liquid distribution layer or to create a liquid distribution layer containing various zones of different levels of fiber alignment. For example, the fibers of a nonwoven web produced by an acute-angle depositing process can be further aligned by a neck-stretching process to produce a highly aligned liquid distribution layer.

Figure 6:
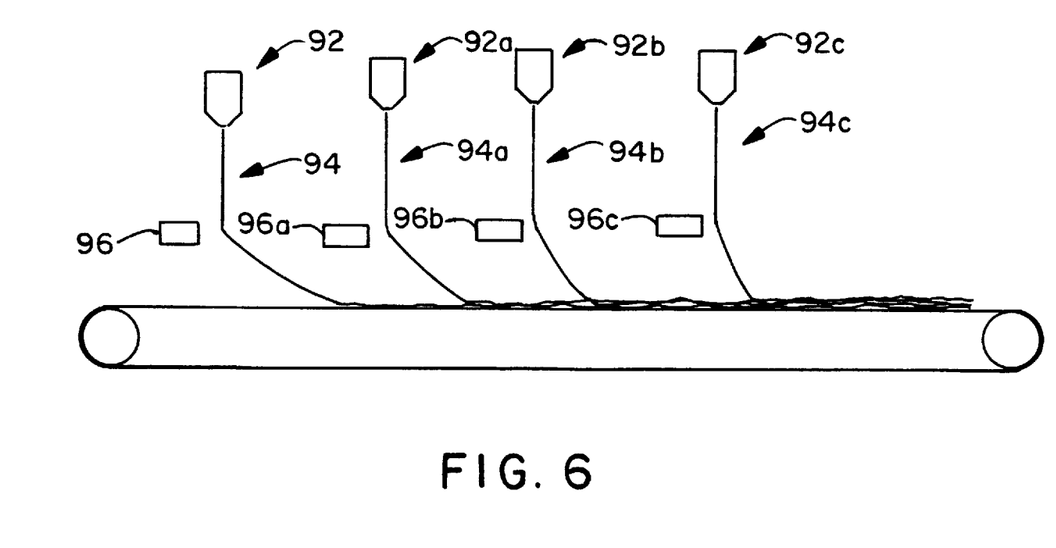
FIG. 6 illustrates a process for producing the liquid distribution layer having a fiber thickness gradient and a fiber orientation gradient.

As stated above, the liquid distribution layer web may further contain a fiber thickness gradient and/or a fiber orientation gradient. A liquid distribution layer having a fiber thickness gradient can be formed by sequentially depositing two or more layers of fibers of different sizes onto a forming surface. At the same time or independently, different levels of fiber orientation can be imparted to each layer by simply incorporating one or more of the above-described fiber orientation processes to impart different fiber orientation levels. Alternatively, liquid distribution webs having different fiber size and orientation gradients can be produced by laminating liquid distribution layers having varied fiber sizes and/or fiber orientation levels. FIG. 6 illustrates an exemplary process that provides both fiber size and orientation gradients. Spinneret assemblies, 92, 92a, 92b and 92c, sequentially deposit spun fibers of increasing fiber thicknesses, 94, 94a, 94b and 94c, to impart an increasing fiber thickness gradient and the deflecting gas supplies, 96, 96a, 96b and 96c, are arranged to provide decreasing levels of pressure and speed to impart a decreasing orientation gradient in the resulting nonwoven web. A liquid distribution layer produced by such a process exhibits a rapid liquid intake property, which is facilitated by the upper portion of the distribution layer, and a fast distribution property, which is facilitated by the lower portion of the liquid distribution layer.

In addition, different sections of a liquid distribution layer can be designed to have varying liquid transfer rates in the z-direction, i.e., in the thickness direction of an absorbent article, in order to control or limit the rate of liquid transfer and saturation to different sections of an absorbent article. It has been found that the rate of liquid transfer or flow from a fiber web in the z-direction is correlated to the permeability and pores structure of the web, i.e., the larger the pore size, the faster the liquid transfer rate in the z-direction. Consequently, imparting proper combinations of suitable fiber alignment levels and pore sizes to different sections of a liquid distribution layer can promote efficient directional movements of liquid in both the planar directions, x-and y-directions, and the thickness direction, z-direction. For example, a highly efficient liquid distribution layer contains a combination of a decreasing fiber thickness gradient as well as an increasing fiber alignment gradient across its thickness, and can be characterized as having three functionally categorizable sub-layers. It is to be noted that each functional sub-layer may be comprised of multiple fiber web layers. The first sub-layer, which facilitates fast intake of incoming liquid, contains relatively thick fibers, large interfiber pores and a low level of fiber alignment; the second sub-layer, which promotes directional liquid distribution and wicking of the absorbed liquid in the first sub-layer to a wide area, even against gravity, contains thinner fibers, smaller interfiber pores and a substantially higher level of fiber alignment than the first sub-layer; and the third sub-layer, which is in contact with an absorbent layer and regulates the rate of liquid transfer to the absorbent layer, contains yet thinner fibers, smaller interfiber pores and a higher level of fiber alignment than the second sub-layer. The third sub-layer may additionally contain an increasing interfiber pore size gradient and a decreasing fiber alignment gradient toward remote sections of the sub-layer such that the remote sections have a faster capacity for z-directional liquid transfer than the section where the liquid distribution layer takes direct insults of incoming liquids, thereby further improving the speed of directional liquid movement and avoiding premature saturation of the absorbent material located directly underneath the section of direct liquid insult. The liquid transfer rate at the remote sections can also be improved by mechanically altering the interfiber structure, e.g., by puncturing and/or slitting. In addition, the first and second sub-layers may contain a decreasing fiber thickness gradient and an increasing fiber alignment gradient toward remote sections of the sub-layers such that the remote sections have a higher capacity for directional liquid movement. It is to be noted that even when the three sub-layers contain sectional fiber size and alignment gradients the average thickness of the thinnest fibers in an upper sub-layer should be larger than the average thickness of thickest fibers in the subjacent sub-layer, and the highest level of fiber alignment in the upper sub-layer should be lower than the lowest level of fiber alignment in the subjacent sub-layer.

The liquid distribution layer of the present invention is fabricated from a synthetic polymer, a natural polymer or a mixture thereof that is known to be suitable for forming fibers. Suitable synthetic polymers include polyolefins, polyamides, polyesters, polycarbonate, acrylic polymers, vinyl acetate-based polymers, polyvinyl chloride, polystyrene and the like, as well as blends and copolymers thereof. Polyolefins suitable for the present invention include polyethylenes, e.g., high density polyethylene, medium density polyethylene, low density polyethylene and linear low density polyethylene; polypropylenes, e.g., isotactic polypropylene and syndiotactic polypropylene; polybutylenes, e. g., poly (1-butene) and poly (2-butene) ; polypentenes, e.g., poly(2-pentene), and poly(4-methyl-1-pentene); and copolymers thereof, e.g., ethylene-propylene copolymer; as well as blends thereof. Of these, more desirable polyolefins are polypropylenes and polyethylenes, more particularly, isotactic polypropylene, high density polyethylene, and linear low density polyethylene. Suitable vinyl acetate-based polymers include polyvinyl acetate; ethylene-vinyl acetate; saponified polyvinyl acetate, i.e., polyvinyl alcohol; ethylene-vinyl alcohol and blends thereof. Suitable polyamides include nylon 6, nylon 6/6, nylon 10, nylon 4/6, nylon 10/10, nylon 12, hydrophilic polyamide copolymers such as caprolactam and alkylene oxide, e.g., ethylene oxide, copolymers and hexamethylene adipamide and alkylene oxide copolymers, and blends and copolymers thereof. Suitable polyesters include polyethylene terephthalate, polybutylene terephthalate, polycyclohexylenedimethylene terephthalate, and blends and copolymers thereof. Acrylic polymers suitable for the present invention include polymethyl methacrylate, ethylene acrylic acid, ethylene methacrylic acid, and the like; and the like as well as blends and copolymers thereof. Suitable natural polymers include modified cellulose such as cellulose acetate, cellulose acetate butyrate, regenerated cellulose and crosslinked polysaccharide. In addition, the fiber composition may further contain minor amounts of compatibilizing agents, colorants, pigments, abrasion resistance enhancing agents, crimp inducing agents, fillers and the like.

The fibers of the liquid distribution layer are modified, especially when hydrophobic polymers are employed, with one or more of wetting agents or surfactants known in the art to suitably impart hydrophilicity and/or liquid wetting properties to the above-illustrated fiber-forming polymers. Alternatively, the liquid distribution layer can be hydrophilically modified after the layer is fully formed, for example, by topically applying a suitable wetting agent. According to the present invention, even inherently hydrophilic polymers may be modified with one or more of wetting agents or surfactants in order to further improve the hydrophilicity of the fibers and fiber webs produced from the polymers. Suitable wetting agents may be internal wetting agents, i.e., wetting agents that are added to the polymer composition prior to spinning or forming fibers therefrom, or topical wetting agents, i.e., agents that are topically applied during or subsequent to the formation of fibers or nonwoven webs. Depending on the uses of absorbent articles, the wetting agent may be fugitive, i.e., the agent will wash off from the fibers when exposed to a minimal number of liquid insults, or nonfugitive, i.e., the agent will durably adhere to the surface of the fibers to withstand two or more of liquid insults. Illustrative examples of suitable wetting agents include silicon based surfactants, e.g., polyalkyleneoxide modified polydimethyl siloxane; fluoroaliphatic surfactants, e.g., perfluoroalkyl polyalkylene oxides; and other surfactants, e.g., actyl-phenoxypolyethyoxy ethanol non-ionic surfactants, alkylaryl polyether alcohols, and polyethylene oxides. Commercially available wetting agents suitable for the present invention include various poly/ethylene oxide) based surfactants available under the tradename Triton, e.g., grade X-102, from Rohm and Haas Crop, various polyethylene glycol based surfactants available under the tradename Emerest, e.g., grades 2620 and 2650, from Emery Industries, various polyalkylene oxide modified polydimethylsiloxane based surfactants available under the tradename Silwet, e.g., grade Y12488, from Union Carbide, fluoroaliphatic surfactants available from 3M, e.g. FC1802, and alkenyl succinamide surfactants available under the tradename Lubrizol, e.g, grade OS85870, from Lubrizol Crop. The amount of wetting agents required and the hydrophilicity of modified fibers for each application will vary depending on the type of wetting agent and the design of absorbent articles.

The liquid distribution layer of the present invention is highly useful for absorbent articles, e.g., diapers, sanitary napkins, training pants, incontinent care products, wound dressings and the like. The liquid distribution layer facilitates better utilization of the absorbent materials and prevents premature failure of absorbent articles while providing physical integrity and dimensional stability.

The present invention is further described with the following examples. The examples are in no way intended to limit the scope of the invention.

EXAMPLES

The directional liquid transfer efficiency of each test specimen was determined by a liquid transfer test (LTT). Each test specimen was cut to strips of a 2 inch width and a 7 inch length and weighed. 2 inches of one end of the strip was laid on a flat platform and a 2 inch cube of an absorbent, which contained 50/50 admixture, by weight, of a wood fluff and a hydrocolloid superabsorbent, was placed over the strip on the platform and a compression force of 0.25 psi was applied on the absorbent. The height of the reservoir was adjusted to make the distance between the top edge of the platform and the top surface of a reservoir of an artificial blood bank saline solution of 0.9% sodium chloride to be 4 inches and the remainder of the strip was vertically dropped into the reservoir, submerging 1 inch of the strip into the saline solution. The strip was allowed to vertically transfer the saline solution to the absorbent for 60 minutes. The performance of each specimen was expressed by the ratio of the weight of the saline solution transferred from the reservoir over the initial weight of the strip.

Example 1 (Ex1)

A polypropylene meltblown fiber web having a basis weight of 50 grams per square meter (GSM) and an average fiber size of about 3.2 μm was produced from polypropylene having a melt flow rate of 400, which was obtained from Himont, grade PF015. The web was hydrophilically modified by spray applying a 4% aqueous solution of an alkenyl succinamide salt, Lubrizol OS85870, which is available from Lubrizol Corp., Ohio, during the fiber spinning process. The web is then neck stretched using the process illustrated in FIG. 5. The steam cans were about 24 inches in diameter and were heated to about 235° F. The linear speed of the web at the first nip was about 37 feet per minute (FPM), at the heated rolls was about 45 FPM and at the second nip was about 75 FPM, producing a 50% neck-stretched web. The neck-stretched web had a 40.4:1 MD:CD fiber alignment ratio. The neck-stretched web was tested for its directional liquid transfer efficiency with the above-described test. The result is shown in Table 1.

Example 2 (Ex2)

A hydrophilically modified polypropylene meltblown fiber web having a basis weight of 50 grams per square meter (GSM) and an average fiber size of about 4.8 μm was produced and neck-stretched in accordance with the procedures outlined in Example 1, except the linear speed of the web at the first nip was about 44 FPM, at the heated rolls was about 50 FPM and at the second nip was about 63 FPM, producing a 30% neck-stretched web. The neck-stretched web had a 13.5:1 MD:CD fiber alignment ratio. The neck-stretched web was tested for its directional liquid transfer efficiency and the result is shown in Table 1.

Controls 1–2 (C1–C2)

Controls 1 and 2 are the hydrophilically modified meltblown webs of Example 1 and 2, respectively, before the webs were subjected to the neck-stretching process. The MD:CD alignment ratios for Controls 1 and 2 were 2.1:1 and 1.3:1, respectively.

TABLE 1

| Example | LTT (g/g @ 60 min) | Alignment Ratio (MD:CD) |
| --- | --- | --- |
| EX 1 | 21.2 | 40.4:1 |
| C1 | 13.9 | 2.1:1 |
| Ex 2 | 12.3 | 13.5:1 |
| C2 | 9.9 | 1.3:1 |

The results demonstrate that the hydrophilically treated, aligned microfiber webs of the present invention efficiently distribute liquid even against the gravitational force. The results also demonstrates that a high level of fiber orientation and a small fiber size in combination provide a highly improved liquid distribution property. In addition, it can be seen from Example 2 and Control 1, which exhibited similar liquid transfer values despite the difference in the fiber thickness, that aligning the fibers of a nonwoven web can impart an improved liquid distribution property comparable to that of a finer fiber nonwoven web.

Example 3

A hydrophilically modified polypropylene liquid distribution layer containing a fiber thickness gradient and a fiber alignment gradient was produced using a meltblown web forming apparatus having four meltblown fiber spinnerets in series, as illustrated in FIG. 6. The polymer through-put values for the first through fourth spinnerets were 2, 2.5, 3 and 3.5 pounds per inch-hour (PIH) and the attenuating air streams for the four spinnerets had 1.8, 1.8, 1.8 and 1.3 psi, respectively. The deflecting air streams for the four fiber streams were supplied at a pressure of about 4.5 inches of water column. The spinneret dies were kept at about 9 inches from the forming surface, and the deflecting air streams were applied at about 5.5 inches above the forming surface and about 3 inches away form the center of the gas-borne fiber streams. The resulting meltblown fiber web had a basis weight of 150 GSM and the average diameters of the fibers of the four sub-layers were 3.8μ, 5.4μ, 5.7μ and 9.5μ, respectively.

The four sub-layers of the meltblown fiber web contained a decreasing fiber thickness gradient as well as an increasing fiber alignment gradient in the direction of its thickness. Although the four deflecting air streams were kept at the same pressure, the differences in the fiber diameter resulted in different levels of fiber alignment. The top surface of the resulted meltblown fiber web, having the thickest fibers, had a 3.2:1 MD:CD fiber alignment ratio and the bottom surface, having the thinnest fibers, had a 5.6:1 MD:CD fiber alignment ratio.

The gradient-containing meltblown fiber web was placed over a blotter paper on a flat, horizontal surface, facing the large fiber side up. The blotter paper was placed under the web to act as an absorbent and to avoid pooling of the saline solution at the bottom of the web. 10 ml of the above-described saline solution was applied at the center of the web and the flow pattern of the saline solution was observed. The saline solution was distributed in an elliptical pattern, unlike a radial, circular liquid distribution pattern of a typical isotropic nonwoven web. The saline solution was distributed to an ellipse of 11.5 cm×7.5 cm in 1 minute. The elliptical distribution of the saline solution clearly demonstrates that the nonwoven web preferentially directs the applied fluid in the direction of fiber alignment.

The anisotropic microfiber web of the present invention provides highly improved liquid distribution properties in the direction of fiber alignment without the problems of prior art liquid distribution layers such as loose and shifting filaments and weak dimensional stability.

What is claimed is:

1. An absorbent article comprising a liquid-permeable facing layer, a liquid distribution layer, an absorbent core and a liquid-impermeable backing layer, wherein said liquid distribution layer comprises a nonwoven web of substantially continuous hydrophilic microfibers, said nonwoven web having a machine direction and a cross-machine direction and first and second planar surfaces, said microfibers having been substantially aligned along said machine or cross-machine direction of said web, said nonwoven web having an increasing fiber alignment gradient and a decreasing fiber thickness gradient in the direction of the web thickness such that said second surface has a higher level of fiber alignment than said first surface and the average diameter of the fibers of said first surface is larger than the average diameter of the fibers of said second surface.

2. A liquid distribution layer for absorbent articles comprising a nonwoven web of substantially continuous hydrophilic microfibers, said microfibers being substantially aligned along one planar dimension of the web, said web having two planar surfaces, wherein said web has an increasing fiber alignment gradient in the direction of the web thickness such that one of said planar surfaces has a higher level of fiber alignment than the other surface.

3. The liquid distribution layer of claim 2 wherein said layer has a fiber alignment ratio of at least about 4:1.

4. The liquid distribution layer of claim 2 wherein said web further comprises a decreasing fiber thickness gradient in the direction of the web thickness such that the average diameter of the fibers of one of said planar surfaces is larger than the average diameter of the fibers of the other planar surface.

* * * * *